US010156615B2

United States Patent
Habara et al.

(10) Patent No.: US 10,156,615 B2
(45) Date of Patent: Dec. 18, 2018

(54) MAGNETIC RESONANCE IMAGING APPARATUS, Q-VALUE CALCULATION METHOD, AND SPECIFIC ABSORPTION RATE MANAGEMENT METHOD

(71) Applicant: HITACHI, LTD., Tokyo (JP)

(72) Inventors: Hideta Habara, Tokyo (JP); Yoshihisa Soutome, Tokyo (JP); Masahiro Takizawa, Tokyo (JP); Yoshiaki Sato, Tokyo (JP)

(73) Assignee: HITACHI, LTD., Tokyo (JP)

( * ) Notice: Subject to any disclaimer, the term of this patent is extended or adjusted under 35 U.S.C. 154(b) by 142 days.

(21) Appl. No.: 15/318,891

(22) PCT Filed: Jun. 23, 2015

(86) PCT No.: PCT/JP2015/067997
§ 371 (c)(1),
(2) Date: Dec. 14, 2016

(87) PCT Pub. No.: WO2016/009791
PCT Pub. Date: Jan. 21, 2016

(65) Prior Publication Data
US 2017/0146620 A1 May 25, 2017

(30) Foreign Application Priority Data
Jul. 14, 2014 (JP) ................................. 2014-144054

(51) Int. Cl.
*G01R 33/28* (2006.01)
*A61B 5/055* (2006.01)
*G01R 33/36* (2006.01)

(52) U.S. Cl.
CPC ............ *G01R 33/288* (2013.01); *A61B 5/055* (2013.01); *G01R 33/3607* (2013.01)

(58) Field of Classification Search
CPC ............ G01R 33/288; G01R 33/34046; G01R 33/543; G01R 33/34007; G01R 33/3415;
(Continued)

(56) References Cited

U.S. PATENT DOCUMENTS 9,864,021 B1 * 1/2018 Habara ................ G01R 33/288
2006/0158191 A1 * 7/2006 Ludwig ............ G01R 33/34046
324/318
(Continued)

FOREIGN PATENT DOCUMENTS

JP         1-210857      8/1989
JP         11-253416     9/1999
(Continued)

OTHER PUBLICATIONS

Frequency Response Resonance Bandwidth Q Factor.*
International Search Report in connection with PCT/JP2015/067997.

*Primary Examiner* — Ruifeng Pu
(74) *Attorney, Agent, or Firm* — Cooper & Dunham LLP

(57) ABSTRACT

Provided is a technique that enables accurate SAR management using power consumption by an object ($P_{object}$) that was calculated based on accurately acquired Q-factors. For this purpose, the present invention calculates Q-factors of each channel of a high-frequency antenna using measurement results of amplitudes of forward waves and reflected waves of each high-frequency signal between three or more different frequencies. An existing SAR monitor in an MRI apparatus is used for the amplitude measurement. Also, the Q-factors are calculated based on a circuit coefficient to be acquired by fitting the measurement results to a predetermined circuit model. Then, the power consumption by an object ($P_{object}$) is calculated using the calculated Q-factors in order to manage the SAR.

12 Claims, 11 Drawing Sheets

(58) Field of Classification Search
CPC .... G01R 33/3453; G01R 33/36; G01R 33/33; G01R 33/3671; G01R 33/443; G01R 33/58; G01R 33/583
See application file for complete search history.

(56) References Cited

U.S. PATENT DOCUMENTS

| | | | |
|---|---|---|---|
| 2007/0182414 A1* | 8/2007 | Morich | G01R 33/34046 324/318 |
| 2011/0148411 A1* | 6/2011 | Bottomley | G01R 33/288 324/309 |
| 2011/0181287 A1* | 7/2011 | Ito | A61B 5/055 324/318 |
| 2014/0232401 A1* | 8/2014 | Takagi | G01R 33/56 324/309 |
| 2015/0268321 A1* | 9/2015 | Zhai | G01R 33/288 324/309 |

FOREIGN PATENT DOCUMENTS

| | | |
|---|---|---|
| WO | WO2010/041706 A1 | 4/2010 |
| WO | WO2014/080781 A1 | 5/2014 |

* cited by examiner (a)

| case | Num. of Fitting points | L [pH] | R [ohm] | C [nF] | |Z| [ohm] | $f_0$ [MHz] | Q | Fit deviation |
|---|---|---|---|---|---|---|---|---|
| Unloaded (empty) | 11 | 436 | 0.00127 | 3.81 | 90.2 | 123.54 | 267 | 0.0005 |
| | 3 | 434 | 0.00124 | 3.83 | 91.7 | 123.62 | 272 | 0 |
| Medium loaded | 11 | 444 | 0.00237 | 3.74 | 50.1 | 123.51 | 145 | 0.0068 |
| | 3 | 445 | 0.0023 | 3.74 | 3.74 | 123.47 | 150 | 0.0021 |
| Highly loaded | 11 | 460 | 0.00681 | 3.82 | 18.6 | 123.22 | 52.3 | 0.0002 |
| | 3 | 448 | 0.00644 | 3.72 | 18.7 | 123.21 | 53.9 | 0 |

800

MAGNETIC RESONANCE IMAGING APPARATUS, Q-VALUE CALCULATION METHOD, AND SPECIFIC ABSORPTION RATE MANAGEMENT METHOD

TECHNICAL FIELD

The present invention relates to a magnetic resonance imaging (hereinafter, referred to as MRI) technique for irradiating high-frequency signals (hereinafter, referred to as Radio Frequency Signals: RF signals) to an object, measuring nuclear magnetic resonance (hereinafter, referred to as NMR) signals from hydrogen, phosphorus, and the like in the object, and images substance density distribution, relaxation time distribution, and the like, and, in particular, to a technique for controlling a human body absorption rate of the RF signals and a SAR (Specific Absorption Rate).

BACKGROUND ART

An MRI apparatus irradiates RF signals that are electromagnetic waves to an object disposed in a homogeneous static magnetic field generated by static magnetic field magnets, excites nuclear spin in the object, receives NMR signals that are electromagnetic waves to be generated by the nuclear spin, and performs signal processing in order to image the object. The RF signal irradiation and the NMR signal reception are performed by an antenna or an antenna device referred to as an RF coil (hereinafter, referred to as an RF antenna) that transmits and receives radio-frequency electromagnetic waves.

Since RF signals are irradiated to an object, the MRI apparatus needs to be controlled so as not to increase the object temperature due to the RF signals and get burned. Therefore, a SAR that is a human body absorption rate of radio waves (specific absorption rate) is managed strictly and accurately. This is referred to as SAR management. In an MRI apparatus of three teslas or more, normally, the SAR management is made by monitoring irradiation power of the RF signals in real time using a SAR monitor.

Irradiation power ($P_{input}$) of RF signals to be input to the RF antenna is represented by the sum of that causes heat generation of the RF antenna due to consumption in the RF antenna (power consumption by the antenna: $P_{antenna}$) and that causes heat generation of an object due to consumption in the object (power consumption by the object: $P_{object}$).

$$P_{input} = P_{antenna} + P_{object} \quad (1)$$

In order to perform accurate SAR management, it is required to grasp the power consumption by the object $P_{object}$. The power consumption by the object $P_{object}$ can be calculated using, for example, Q-factors of resonance of the RF antenna. That is, a Q-factor ($Q_{empty}$) in a state where the object (patient) is not inside the RF antenna and a Q-factor ($Q_{loaded}$) in a state where the object is inside the RF antenna are measured and obtained, and the values are used for calculation by the following equation (2) (for example, refer to Patent Literature 1).

$$P_{object} = P_{input} \times (1 - Q_{loaded}/Q_{empty}) \quad (2)$$

CITATION LIST

Patent Literature

PTL 1: U.S. Pat. No. 8,102,177B2

SUMMARY OF INVENTION

Technical Problem

A recent MRI apparatus tends to increase the number of transmission channels of the RF antenna to 2 to 16 channels. By providing a plurality of the transmission channels, irradiation power and a phase are changed in each channel, which helps irradiation to be spatially homogenized. In a case of using an RF antenna provided with a plurality of channels, Q-factors are measured in all the channels, and calculation needs to be performed using the equations (1) and (2) in order to evaluate accurate power consumption by the object $P_{object}$.

In order to measure Q-factors of the antenna, normally, forward waves and reflected waves need to be measured including the phases in a state where a patient is actually disposed using an expensive dedicated device such as a network analyzer. However, it is financially difficult to install the expensive dedicated device in an MRI apparatus. Also, Q-factor measurement is performed in addition to normal imaging operation, which results in a long constraining time for the patient.

A SAR can be estimated without the Q-factor measurement by assuming that all the power sent to the RF antenna is supplied to an object. In this case, the SAR is estimated excessively, and restriction of the imaging sequence is increased, which extends an imaging time than usual.

The present invention was made in light of the above problems and provides a technique that enables accurate SAR management using power consumption by an object $P_{object}$ that was calculated based on accurately acquired Q-factors without installing an expensive measuring device and extending an imaging time extremely.

Solution to Problem

In the present invention, Q-factors of each channel of a high-frequency antenna are calculated using measurement results of amplitudes of forward waves and reflected waves of each high-frequency signal between three or more different frequencies. An existing SAR monitor in an MRI apparatus is used for the amplitude measurement. Also, the Q-factors are calculated based on a circuit coefficient to be acquired by fitting the measurement results to a predetermined circuit model. Then, the power consumption by an object $P_{object}$ is calculated using the calculated Q-factors in order to manage the SAR.

Advantageous Effects of Invention

According to the present invention, accurate SAR management can be performed using power consumption by an object $P_{object}$ that was calculated based on accurately acquired Q-factors without installing an expensive measuring device and extending an imaging time extremely.

BRIEF DESCRIPTION OF DRAWINGS

FIG. 11 illustrates calculation results in a practical example of the present invention.

DESCRIPTION OF EMBODIMENTS

Hereinafter, an example of an embodiment to which the present invention is applied will be described. In all the drawings illustrating the embodiments of the present invention, the same reference signs are used for the same functions, and the repeated descriptions are omitted unless otherwise stated.

[Configuration of MRI Apparatus]

Figure 1:
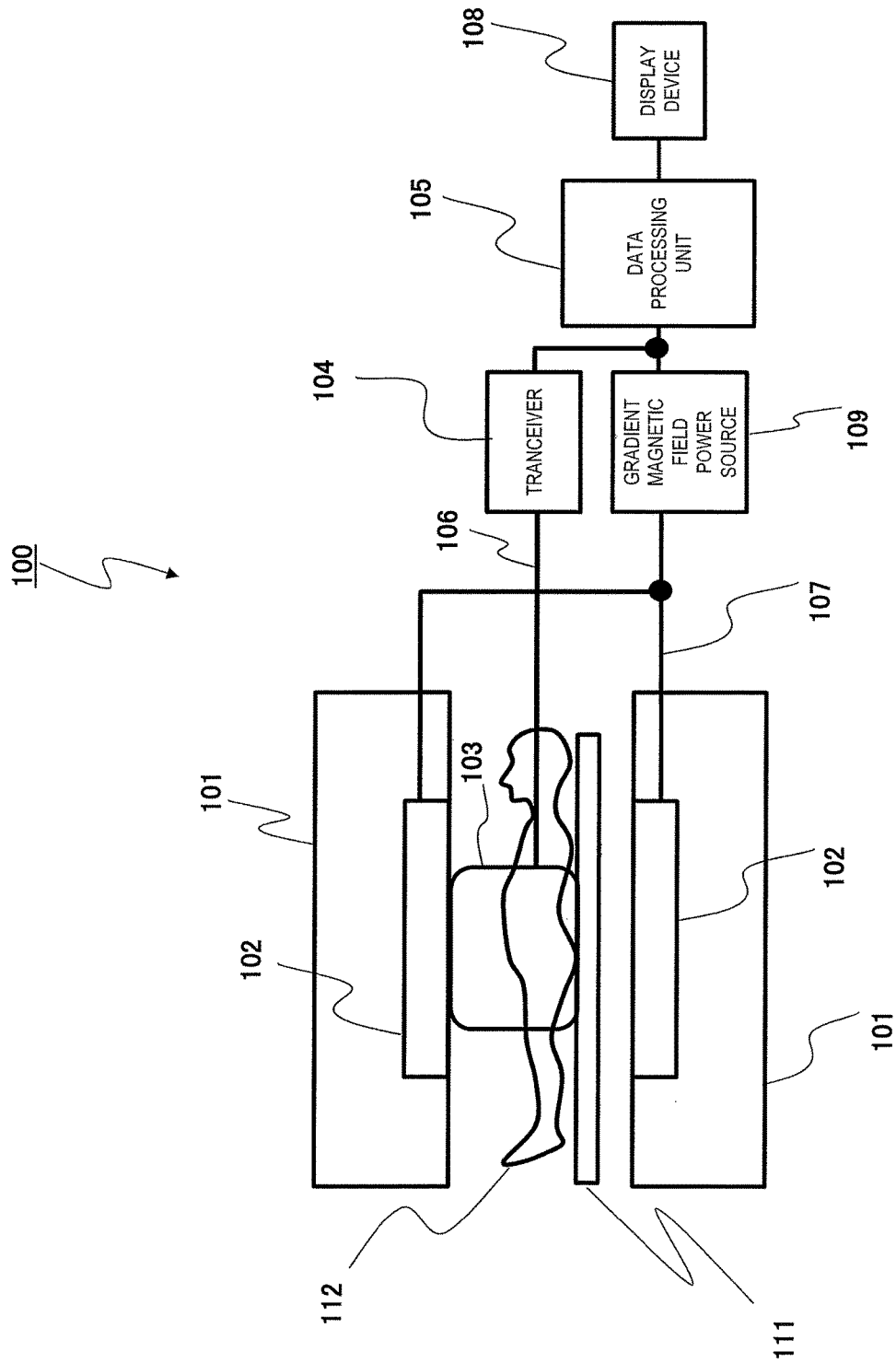
FIG. 1 is an overall configuration diagram of an MRI apparatus in embodiments of the present invention.

First, the MRI apparatus configuration of the present invention will be described. FIG. 1 is the overall configuration diagram of an MRI apparatus 100 of the present embodiment. The MRI apparatus 100 is provided with magnets 101 that forms a static magnetic field in a measurement space in which an object 112 is disposed; gradient magnetic field coils 102 that provides a magnetic field gradient in a predetermined direction to the static magnetic field; an RF antenna 103 that transmits high-frequency signals (RF signals) to the object 112 and receives nuclear magnetic resonance signals (NMR signals) to be generated from the object 112; a transceiver 104 that generates the RF signals (RF waves) to be transmitted from the RF antenna 103 before transmitting to the RF antenna 103 and performs signal processing on the NMR signals received by the RF antenna 103; a gradient magnetic field power source 109 that supplies electric current to the gradient magnetic field coils 102; a data processing unit 105 that controls driving of the transceiver 104 and the gradient magnetic field power source 109 and receives various information processes and operations by an operator; a display device 108 for displaying processing results by the data processing unit 105; and a bed 111 on which the object 112 is placed.

The gradient magnetic field power source 109 and the gradient magnetic field coils 102 are connected with a gradient magnetic field control cable 107. Also, the RF antenna 103 and the transceiver 104 with transmission/reception cables 106 that transmit and receive signals between the RF antenna 103 and the transceiver 104. Although not illustrated in the drawing, the transceiver 104 is provided with a synthesizer; a power amplifier; a reception mixer; an analog/digital converter; a transmission/reception switch; and the like.

The RF antenna 103 of the present embodiment is a multi-channel antenna that resonates at a predetermined frequency and has one or more channels.

The MRI apparatus 100 is distinguished between a horizontal magnetic field type and a vertical magnetic field type according to a direction of a static magnetic field to be formed by the magnets 101. In a case of the horizontal magnetic field type, the magnets 101 generally have a cylindrical bore (center space), generate horizontal static magnetic fields in FIG. 1, and are referred to as a tunnel-type MRI apparatus. On the other hand, in a case of the vertical magnetic field type, a pair of magnets is vertically disposed across the object 112, and generates vertical static magnetic fields in FIG. 1.

The data processing unit 105 controls the transceiver 104 and the gradient magnetic field power source 109 and irradiates and applies RF signals that are intermittently at intervals of a few milliseconds and gradient magnetic fields respectively to the object 112 disposed in static magnetic fields from the RF antenna 103 and the gradient magnetic field coils 102. Also, NMR signals to be generated from the object 112 by resonating with the RF signals are received with the RF antenna 103, signal processing is performed, and then images are reconstructed. The object 112 is, for example, a predetermined site of the human body.

The data processing unit 105 of the present embodiment further calculates Q-factors of each channel of the RF antenna 103. Then, SAR management during imaging is performed using the calculated Q-factors.

Although FIG. 1 illustrates a single RF antenna as the RF antenna 103 that performs RF signal transmission and NMR signal reception, the configuration is not limited to this. For example, an RF antenna consisting of a plurality of antennas may be used as the RF antenna 103 by combining an RF antenna for wide-range imaging and a local RF antenna, for example. Particularly in a case of imaging each site of the human body in detail, different antennas are frequently used between transmission and reception. Frequently used for the transmission is an irradiation antenna installed inside the gradient magnetic field coils so as to cover the entire body, and frequently used for the reception is a local antenna disposed near the periphery of the human body. In this case, the local antenna is frequently dedicated to the reception.

[Configuration of RF Transmission/Reception System]

Figure 2:
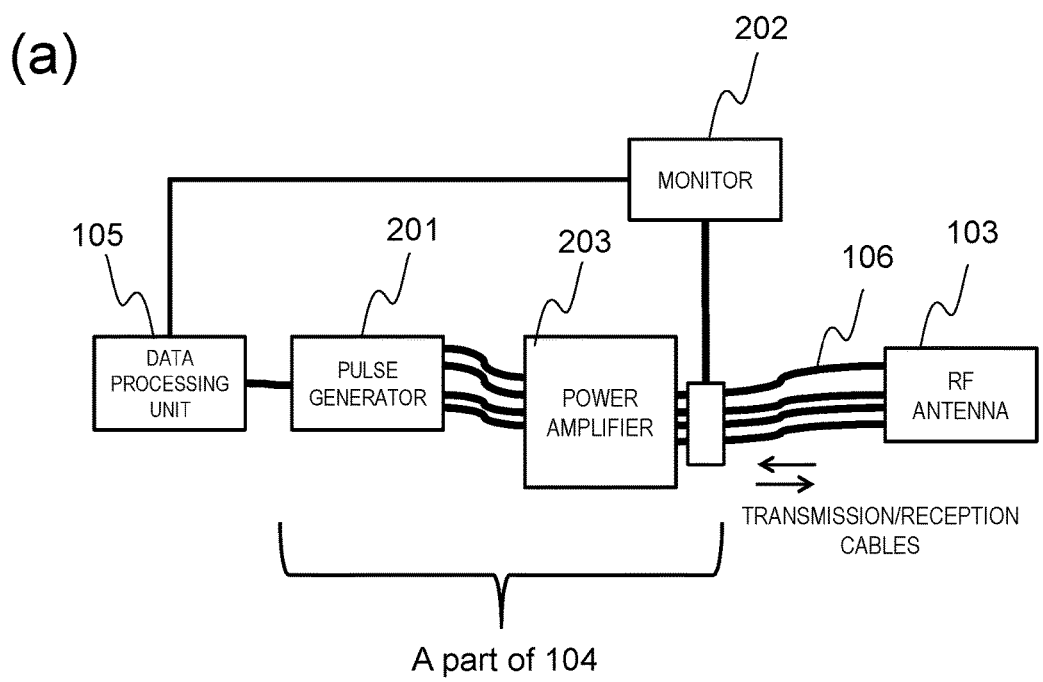
FIG. 2(*a*) is a block diagram of an RF transmission system in the embodiments of the present invention, and FIG. 2(*b*) is a functional block diagram of a data processing unit in the embodiments of the present invention.
Figure 2:
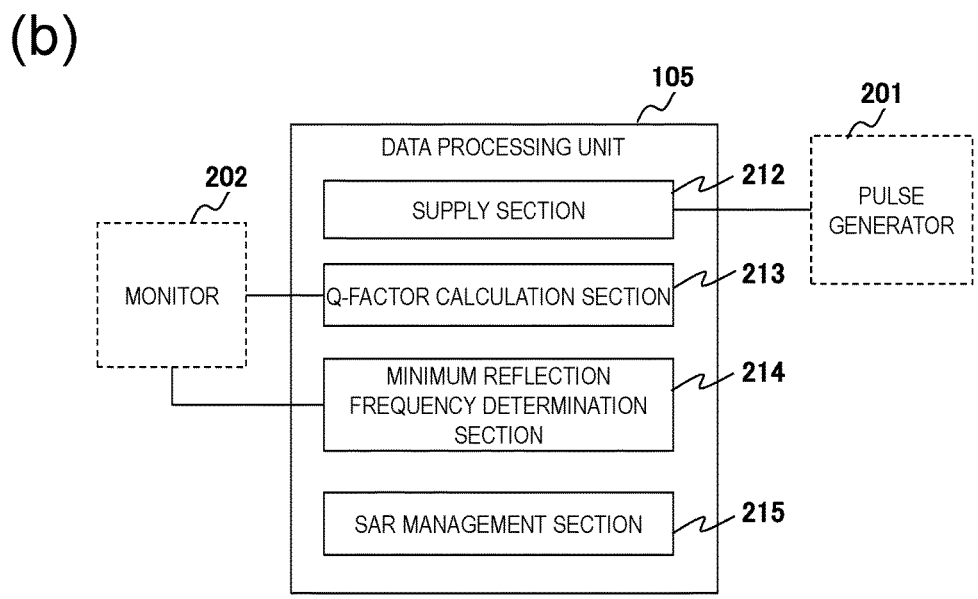

FIG. 2(a) is a detailed block diagram of the data processing unit 105, the transceiver 104, the transmission/reception cables 106, and the RF antenna 103 (RF transmission system) in FIG. 1. As an example, a case where the RF antenna 103 has four channels is illustrated here.

As illustrated in the present drawing, the transceiver 104 of the present embodiment is provided with an RF pulse generator (hereinafter, simply referred to as a pulse generator) 201; a power amplifier 203; and a monitor 202.

The pulse generator 201 generates pulse waves of RF signals (transmission RF pulses) to be transmitted from the RF antenna 103. The transmission RF pulses are generated as signals whose peak power is a few milliwatts and are input in the power amplifier 203. It is noted that the transmission RF pulses are generated for each channel of the RF antenna 103.

The power amplifier 203 amplifies the input transmission RF pulses to RF waves whose peak power is a few kilowatts before transmitting to the RF antenna 103.

The transmission/reception cables 106 are high-voltage RF coaxial cables connecting between the pulse generator 201 and the RF antenna 103 through the power amplifier 203. In the present embodiment, the pulse generator 201 and the RF antenna 103 are connected for each channel. Therefore, the transmission/reception cables 106 are provided by the number of channels. Because the RF antenna 103 has four channels in the example of FIG. 2(a), the RF antenna 103 and the pulse generator 201 are connected by four pieces of the transmission/reception cables 106.

The monitor 202 monitors amplitudes of forward waves and backward waves of high-frequency signals (RF signals) that are disposed immediately after the output of the power amplifier 203 and supplied to the RF antenna 103 through the transmission/reception cables 106. The forward waves are RF signals traveling from the power amplifier 203 to the RF antenna 103, and the backward waves are RF signals traveling backward to the forward waves. The backward waves are made by superimposing reflected waves in which the forward waves are reflected by the RF antenna 103 on waves sneaking from a plurality of the other channels of the RF antenna 103, and the backward waves travel from RF antenna 103 to the power amplifier 203. In a case where transmission is performed through one channel only from among a plurality of the channels, the waves sneaking from the other channels can be reduced to zero. In the present description, a case of measuring reflection coefficients will be considered. Therefore, a case where the backward waves are all the reflected waves will be considered by limiting channels for simultaneous transmission to one channel and assuming that the sneak waves are zero.

The monitor 202 monitors the forward waves and the reflected waves respectively for each channel and outputs the respective amplitudes to the data processing unit 105. Although a case where the monitor 202 is disposed outside the power amplifier 203 is illustrated as an example in FIG. 2(a), the monitor 202 may be built in the power amplifier 203.

[Functional Configuration of Data Processing Unit]

Described next will be a functional configuration of the data processing unit 105 of the present embodiment related to Q-factor calculation and SAR management. In the present embodiment, Q-factors are calculated from amplitudes of forward waves and reflected waves acquired by the monitor 202. In order to realize this, the data processing unit 105 is provided with a supply section 212; a Q-factor calculation section 213; a minimum reflection frequency determination section 214; and a SAR management section 215 as illustrated in FIG. 2(b).

The supply section 212 supplies high-frequency signals (RF signals) to the RF antenna 103. In the present embodiment, the pulse generator 201 is instructed to generate RF pulse waveforms to be supplied to each channel of the RF antenna 103.

The Q-factor calculation section 213 calculates Q-factors of the RF antenna 103 using each amplitude acquired from the monitor 202. In the present embodiment, the Q-factor calculation section 213 calculates Q-factors by fitting absolute values of reflection coefficients acquired from amplitudes of forward waves and reflected waves to a predetermined circuit model. The absolute values of the reflection coefficients are acquired by calculating square roots of values acquired by dividing amplitudes of the reflected waves by amplitudes of the forward waves.

Used for fitting are absolute values of reflection coefficients of RF signals of three or more predetermined different frequencies. For example, used are three frequencies of an upper-limit frequency that the MRI apparatus 100 can use; a lower-limit frequency; and a minimum reflection frequency at which absolute values of reflection coefficients of the RF antenna 103 are the smallest or a plurality of frequencies including these three frequencies. Although the number of the frequencies is not theoretically limited, the practical upper-limit number may be set to approximately 2,000.

The Q-factor calculation section 213 performs a Q-factor calculation process for each of imaging operations, the objects 112, and imaging sites using amplitudes of forward waves and reflected waves measured by the monitor 202 in a state where the object 112 is disposed inside the RF antenna 103 in an embodiment during imaging i.e., a load state during imaging. Therefore, a $Q_{loaded}$ in the above equation (2) can be acquired by the Q-factor calculation section 213.

The minimum reflection frequency determination section 214 determines a minimum reflection frequency by fitting absolute values of reflection coefficients acquired from each amplitude measured by the monitor 202 to a circuit model to be used by the Q-factor calculation section 213. At this time, used are the reflection coefficients of RF signals of four or more predetermined different frequencies. Although the number of the frequencies is not theoretically limited, the practical upper-limit number may be set to approximately 2,000.

The reason why the minimum reflection frequency is previously measured is to increase measurement accuracy in a state where impedances of the RF antenna 103 and the transmission/reception cables 106 are matched (matching state) i.e., in a point where load impedances are close to 50 ohms. The measurement is performed at a load close to 50 ohms. That is, the minimum reflection frequency determination section 214 measures a minimum reflection frequency in the matching state using an appropriate load. Also, the minimum reflection frequency determination section 214 additionally calculates a Q-factor ($Q_{empty}$) of the RF antenna 103 in a state without the load (unloaded state). When the Q-factor is calculated, the measurement is performed in the unloaded state after removing the load.

The minimum reflection frequency determination section 214 determines a minimum reflection frequency at a timing different from imaging. For example, the determination is performed when the MRI apparatus 100 is manufactured, installed, adjusted, maintained, or the like. That is, the determination process of the minimum reflection frequency is performed when the MRI apparatus 100 is installed in a hospital or the like or when parts related to the transmission system such as the power amplifier 203, the RF antenna 103, the transmission/reception switch, the transmission/reception cables 106, or the like is replaced. Also, the process is executed in the unloaded state.

The SAR management section 215 calculates irradiation power (power consumption by an object $P_{object}$) that affects the object 112 from irradiation power ($P_{input}$) by high-frequency signals (RF signals) to be supplied to the high-frequency antenna (the RF antenna 103) during imaging using the Q-factor ($Q_{loaded}$) calculated by the Q-factor calculation section 213 in order to control a specific absorption rate SAR.

In the present embodiment, the power consumption by an object ($P_{object}$) is calculated to calculate a SAR by the above equation (2) using the Q-factor ($Q_{loaded}$) calculated by the Q-factor calculation section 213 and the Q-factor ($Q_{empty}$) calculated by the minimum reflection frequency determination section 214. Then, the SAR management is performed.

The SAR management to be executed by the SAR management section 215 will be described specifically. The SAR management section 215 estimates a SAR and performs control by actual measurement. In order to estimate a SAR, a Q-factor ($Q_{loaded}$) is used. The Q-factor ($Q_{loaded}$) is acquired by measurement using a pre-scan before the main imaging sequence when a position of the object 112 is determined.

The SAR management section 215 estimates a SAR from the acquired Q-factor ($Q_{loaded}$) and waveforms, intensities, and the number of occurrences of RF pulses in the subsequent imaging sequence. Specifically, using the equation (2), power to be supplied to the object 112 from each channel (power consumption by an object $P_{object}$) is calculated to evaluate a 10-second average and a 6-minute average of the sum of the power (power consumption by an object $P_{object}$) to be supplied by all the channels as a SAR. Then, whether or not the calculation results conform to safety standards such as IEC (International Electrotechnical Commission), for example, 3 watts or less per weight of 1 kg, is determined, and if not, the calculation results is controlled so as to conform to the standards.

The SAR management section 215 controls the calculation results so as to conform to the safety standards by setting an interval during imaging for example in a case where the calculation results exceeds the safety standards. Alternatively, the calculation results are controlled for the conformity by changing waveforms, intensities, and the number of occurrences of irradiation RF pulses.

The SAR management section 215 continues measuring irradiation RF waveforms also after main imaging starts and gives a warning or executes emergency stop of the apparatus and the like if the actual measurement exceeds the limit compared to the estimation and some problem occurs in the safety.

[Details of Q-Factor Calculation Process]

Hereinafter, described will be the details of the Q-factor calculation process by the Q-factor calculation section 213 of the present embodiment.

[Forward Waves and Reflected Waves]

Figure 3:
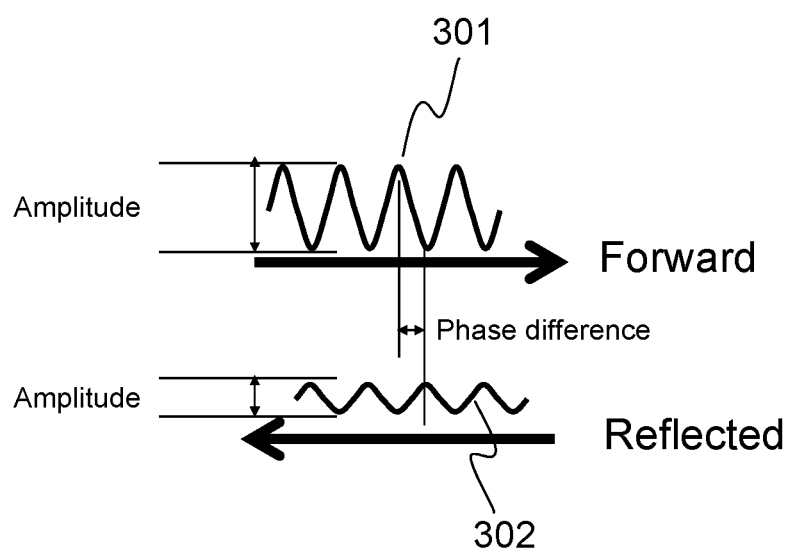
FIG. 3 illustrates amplitudes of forward waves and reflected waves of RF signals and the phase relationship in the embodiments of the present invention.
Figure 4:
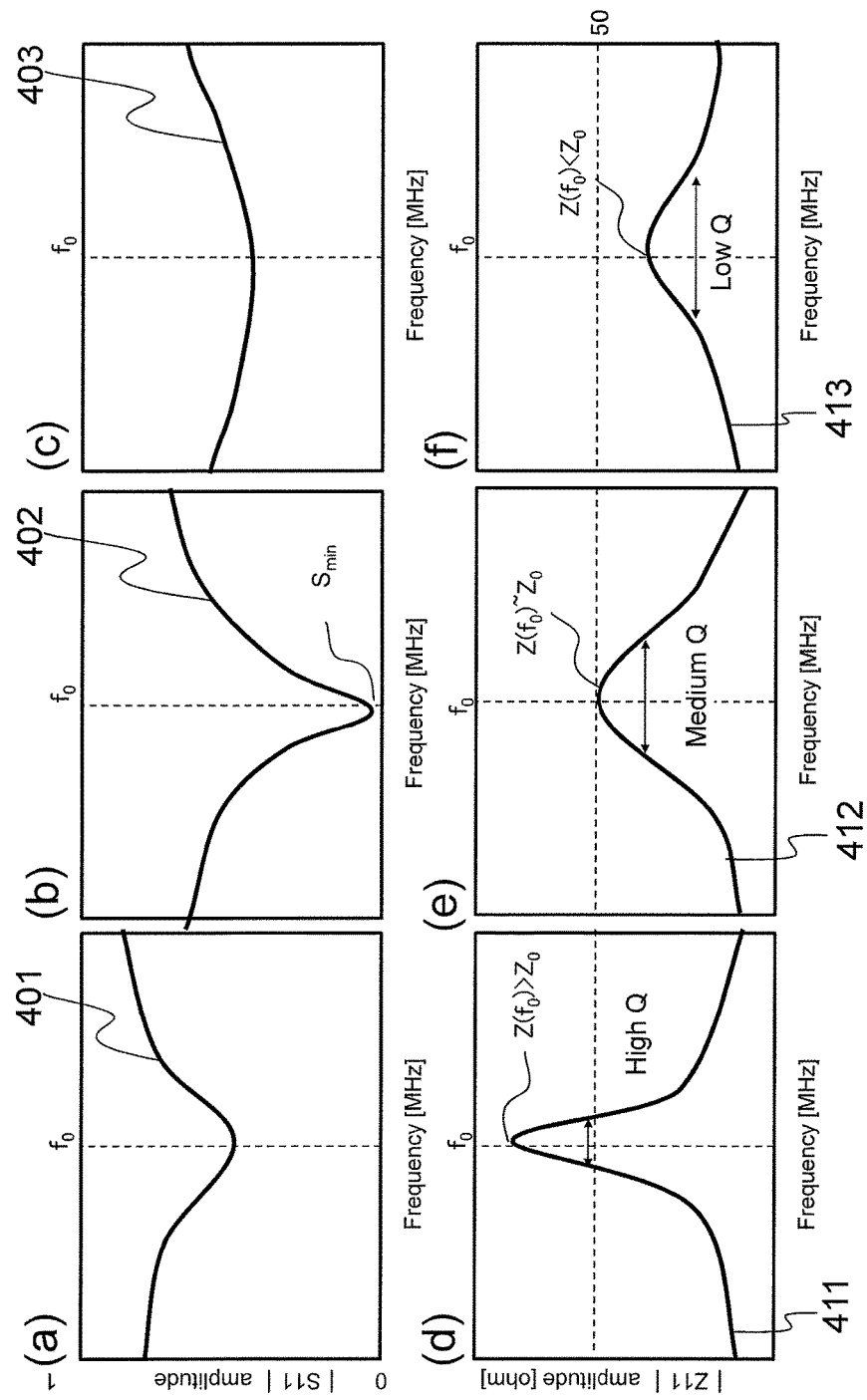
FIGS. 4(a) to 4(c) illustrate changing states of absolute values of reflection coefficients to frequencies in the embodiments of the present invention.
FIGS. 4(d) to 4(f) illustrate changing states of absolute values of impedances to frequencies in the embodiments of the present invention.

First described are the forward waves and the reflected waves measured by the monitor 202. FIG. 3 illustrates RF signals (RF waves) passing through one transmission/reception cable (RF coaxial cable) 106. As described above, the RF waves passing through the transmission/reception cable 106 include the forward waves (input waves: Forward) 301 traveling from the power amplifier 203 to the RF antenna 103 and the reflected waves (Reflected) 302 traveling backward.

As illustrated in the present drawing, the forward waves 301 and the reflected waves 302 include amplitudes and phases respectively. Phase differences are generated between the forward waves 301 and the reflected waves 302.

Normally, coaxial cables 106 of a 50-ohm ($\Omega$) system are used for RF waves from a few MHz to a few hundred MHz to be used for an MRI apparatus. When an input impedance (hereinafter, simply referred to as an impedance) Z of the RF antenna 103 is appropriately matched to 50 ohms, the forward waves 301 hardly reflect. However, if the impedance Z of the RF antenna 103 is deviated from 50 ohms, the reflected waves 302 are generated.

The impedance Z of the RF antenna 103 fluctuates greatly depending on the size, the body composition, and the like of the object (patient) 112 to be disposed inside the RF antenna 103. In a case where a large object 112 is inside the RF antenna 103 or where the object 112 is close to the conductor of the RF antenna 103, a load of the RF antenna 103 becomes high, and the impedance Z is changed (reduced). Therefore, it is difficult to adjust the impedance Z of the RF antenna 103 to 50 ohms in a state during imaging, the reflected waves 302 are generated during actual imaging.

[Q-Factor Calculation Method]

Next, the Q-factor calculation method will be described. A Q-factor of the RF antenna 103 is generally calculated using the following equation (3).

$$Q = \frac{f(z_{max})}{\delta f} \quad (3)$$

Here, $f(Z_{max})$ is a frequency at which an absolute value |Z11| of the impedance Z of the RF antenna 103 (hereinafter, simply referred to as an impedance |Z11|) takes a peak value ($Z_{max}$). Also, of is a value of $1/\sqrt{2}$ of the peak value $Z_{max}$ Of the impedance |Z11| i.e., a difference between two frequencies at which $|Z11|=Z_{max}/\sqrt{2}$ and |Z11| intersect. That is, $\delta f$ is a width of a peak of the impedance |Z11|.

The impedance Z of the RF antenna 103 is represented by the following equation (4-1) using a reflection coefficient S to be calculated from the forward waves 301 and the reflected waves 302.

$$Z = Z_0 \frac{1+S}{1-S} \quad (4\text{-}1)$$

$$S = \frac{Z - Z_0}{Z + Z_0} \quad (4\text{-}2)$$

It is noted that $Z_0$ is a characteristic impedance (normally, 50 ohms) of a system. Also, the equation (4-2) is an equation to convert the impedance Z into the reflection coefficient S.

Since the impedance Z is a complex value, the reflection coefficient S also needs to be acquired as a complex value. Therefore, the forward waves 301 and the reflected waves 302 need to be measured as complex values. That is, in a case of calculating a Q-factor using the above equation (3), not only amplitudes but also phases of the forward waves 301 and the reflected waves 302 need to be measured.

[Monitor Limit]

However, only the respective amplitudes of the forward waves 301 and the reflected waves 302 can be measured by the monitor 202 as described above. This is because the monitor 202 is originally provided in order to monitor a SAR i.e., RF power.

The monitor 202 continues to monitor an RF wave in milliseconds, which enters the RF antenna 103 intermittently while an imaging sequence of an MRI apparatus is being executed, over several tens of minutes. A frequency of an RF wave to be used for a three-tesla MRI apparatus is approximately 128 MHz. In order to reduce a data amount to a processable amount, the monitor 202 is configured so as to integrate detection waveforms in a few microseconds.

In order to directly detect RF-wave phases, the RF waveforms need to be measured with a high time resolution. For example, in order to detect an RF-waveform phase of 128 MHz with a resolution of approximately five degrees, the RF wave needs to be detected in approximately 109 picoseconds, and the detection can be performed by the monitor 202 designed as described above.

For example, detection can be performed by an oscilloscope with a resolution of approximately 100 picoseconds. However, it is not practical to install such an oscilloscope in an MRI apparatus because the oscilloscope is expensive. Also, phase detection can be performed with a method using frequency mixing such as heterodyne detection even after a resolution of the oscilloscope is greatly reduced in the time direction. However, in order to perform the heterodyne detection, a stable medium frequency that is for mixing and referred to as LO (local) needs to be distributed in the detection place, and the system becomes expensive and complicated, which is not practical.

In a case where the forward waves 301 and the reflected waves 302 are continuous waves and an advanced measuring device is used, phase differences can be measured between both the waves. However, RF waves to be normally used for the MRI apparatus 100 have pulse shapes whose lengths are a few milliseconds.

Thus, using a heterodyne detection method in which a complicated configuration is necessary or processing data at a 100-picosecond level is required for the monitor 202 provided in the MRI apparatus 100 as a SAR monitoring system to have a function for detecting phases of the forward waves 301 and the reflected waves 302, which results in a significant cost increase.

[Output Frequency Limit]

A reflection coefficient S is calculated by outputting RF signals with small power after changing the frequencies in a wide range, measuring an amplitude and a phase of a forward wave and a reflected wave for the respective frequencies, and dividing a complex value of the reflected wave by a complex value of the forward wave. Q-factors of the RF antenna 103 of the MRI apparatus 100 fluctuate in a range of approximately 20 to 300 according to the load size. In a case of the three-tesla MRI apparatus 100, it is found that a range (band width) of 6.4 to 0.4 MHz for changing the frequencies is required to measure the Q-factors accurately.

However, the power amplifier 203 and the pulse generator 201 in most MRI apparatuses 100 do not support such a wide band, frequencies cannot be changed within the above range for phase measurement.

The MRI apparatus 100 increases the sensitivity of the RF antenna 103 by resonation. In a case of the three-tesla MRI apparatus 100, the center frequency that the pulse generator 201 generates is set so as to correspond to a resonant frequency $f_H$ of hydrogen nuclear spin, and a resonant frequency $f_0$ of the RF antenna 103 is adjusted so as to fall within a range of ±0.2 MHz of the resonant frequency $f_H$ of hydrogen nuclear spin. Therefore, it is enough that the power amplifier 203 has a narrow band capable of covering this range several times larger, and an expensive wide-band amplifier is not necessarily used. Normally, a band to be used by the power amplifier 203 is approximately ±0.5 MHz. Therefore, the MRI apparatus 100 cannot supply RF waves with a wide frequency range to the RF antenna 103.

Also, an oscillating frequency needs to be finely changed by a few Hz in the MRI apparatus 100. Therefore, a frequency range where the pulse generator 201 can oscillate is approximately $f_0$±1 MHz. Also, a band-pass-type filter is provided in order to remove RF waves that can be noise other than the vicinity of a resonant frequency $f_0$ in the MRI apparatus.

As described above, complex values of the forward waves 301 and the reflected waves 302 cannot be acquired using the function of the transceiver 104 installed in a normal MRI apparatus 100.

[Relationship Between Reflection Coefficient, Impedance, and Q-Factors]

Next, described will be the relationship between a reflection coefficient, an impedance, and a Q-factor. FIGS. 4(a) to 4(f) are the graphs for illustrating the relationship between a reflection coefficient S, an impedance Z, and a Q-factor in one channel of the RF antenna 103.

FIGS. 4(a) to 4(c) are the graphs 401, 402, and 403 respectively illustrating changes of an absolute value |S11| of a reflection coefficient to a frequency (hereinafter, simply referred to as the reflection coefficient |S11|) in a different load state. Here, the vertical axis is the reflection coefficient |S11| (|S11| amplitude), and the horizontal axis is the frequency (Frequency [MHz]). FIGS. 4(d) to 4(f) are the graphs 411, 412, and 413 respectively illustrating changes of an absolute value |Z11| of an impedance Z of the RF antenna 103 to a frequency (impedance |Z11|) in the same load state as FIGS. 4(a) to 4(c). Here, the vertical axis is the impedance |Z11|(|Z11|amplitude [ohm]), and the horizontal axis is the frequency (Frequency [MHz]).

It is noted that a resonant frequency $f_0$ is adjusted so as to correspond to ±0.2 MHz of a resonant frequency $f_H$ of hydrogen nuclear spin of water by a static magnetic field of the MRI apparatus 100. The resonant frequency $f_0$ is close to approximately 128 MHz in a three-tesla MRI apparatus 100.

FIGS. 4(a) and 4(d) are the reflection coefficient |S11| (401) and the impedance |Z11| (411) in a no-load state (unloaded state) in the RF antenna 103. The reflection coefficient |S11| at a resonant frequency $f_0$ is closer to 1 than 0. Then, the impedance |Z11| exceeds 50 ohms at the peak.

Also, FIGS. 4(b) and 4(e) are the reflection coefficient |S11|(402) and the impedance |Z11|(412) in an intermediately (appropriately) loaded state (medium load state) in the RF antenna 103. In the medium load state, the impedance Z of the RF antenna 103 is matched with 50 ohms at a resonant frequency $f_0$. In the medium load state, the reflection coefficient |S11|(402) gets close to 0 at the resonant frequency $f_0$, and the peak of the impedance |Z11|(412) becomes 50 ohms.

Also, FIGS. 4(c) and 4(f) are the reflection coefficient |S11| (403) and the impedance |Z11| (413) in a state with a large load (high loaded state) in the RF antenna 103. The reflection coefficient |S11| (403) at the resonant frequency $f_0$ gets closer to 1 than 0, and the peak of the impedance |Z11| (413) is lower than 50 ohms.

In FIGS. 4(a) to 4(c), a frequency $f(S_{min})$ indicates frequencies at the minimum points of the respective graphs 401, 402, and 403 that are downward convex curves. Hereinafter, the frequencies at the minimum points are referred to as minimum reflection frequencies. In a case of a normal RF antenna 103 of the MRI apparatus 100, a minimum reflection frequency $f(S_{min})$ is adjusted so as to correspond to a resonant frequency $f_H$ of hydrogen nuclear spin within a difference of ±0.2 MHz.

In FIGS. 4(d) to 4(f), $f(Z_{max})$ indicates frequencies at the maximum points of the respective graphs 411, 412, and 413 that are upward convex curves. Phase offsets are normally adjusted so that $f(Z_{max})$ and a minimum reflection frequency $f(S_{min})$ correspond when a reflection coefficient |S11| is measured.

According to the above equation (3), an impedance Z of the port of the RF antenna 103, and Q-factors are also high (High Q) because a width of the peak of the impedance |Z11| is narrow in the unloaded state illustrated in FIGS. 4(a) and 4(d). Inversely, Q-factors are low (Low Q) in the high loaded state illustrated in FIGS. 4(c) and 4(f). Then, Q-factors are medium values (Medium Q) between both the above states in FIGS. 4(b) and 4(e).

It is noted that converting S into Z cannot be easily performed using the equations (4-1) and (4-2) in a case where phase information of a reflection coefficient S cannot be acquired and only an absolute value |S11| can be measured. In a High Q case (401) illustrated in FIG. 4(a) and a Low Q case (403) illustrated in FIG. 4(c), it is difficult to distinguish both the cases because they resemble each other when only |S11| is focused. Therefore, it is difficult to calculate Q-factors easily.

Figure 5:
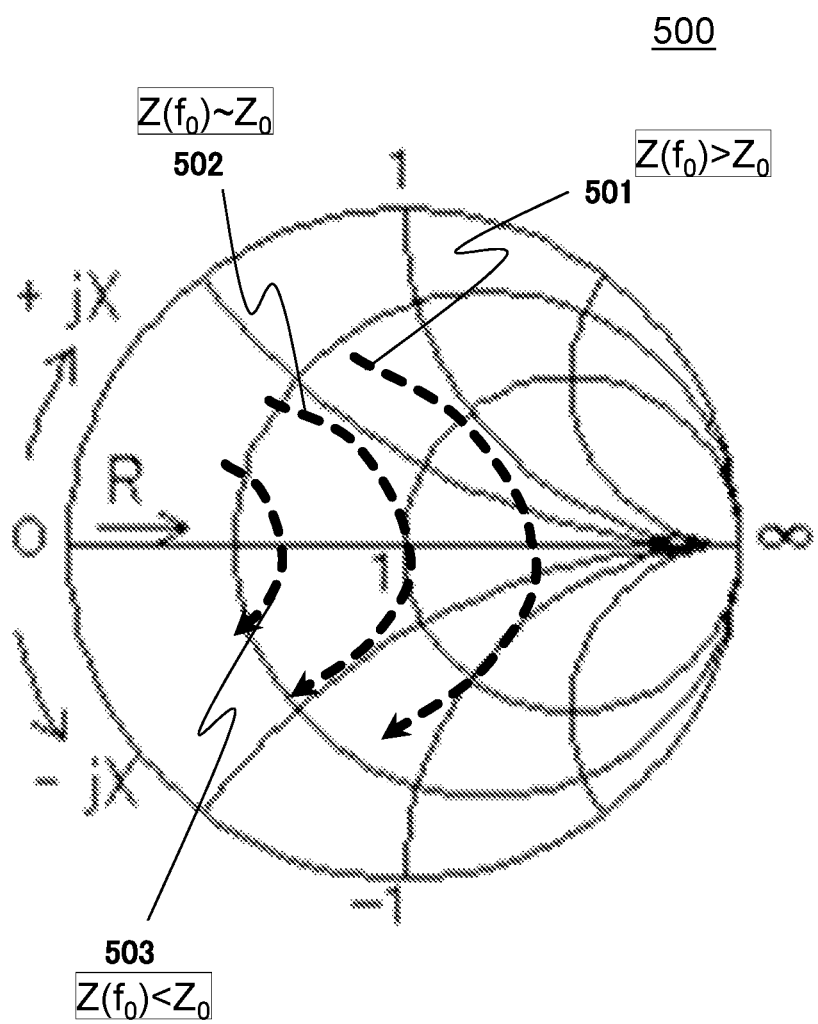
FIG. 5 is a Smith chart illustrating changing states of the reflection coefficients and the impedances indicated in FIGS. 4(a) to 4(f).

FIG. 5 is a Smith chart 500 illustrating each state of FIGS. 4(a) to 4(f). In a case of the medium load (Medium Q) illustrated in FIGS. 4(b) and 4(e) in which the peak of the impedance Z is matched with approximately 50 ohms, the impedance Z at the center frequency $f(Z_{max})$ becomes approximately $Z_0$ ($Z(f_0)$ to $Z_0$), and a curve 502 of an S parameter (reflection coefficient S) becomes an arc-shaped curve passing through the center on the Smith chart 500.

In a case of the unloaded (High Q) state illustrated in FIGS. 4(a) and 4(d), Q-factors become large, and the impedance Z at the center frequency $f(Z_{max})$ is higher than $Z_0$ ($Z(f_0)>Z_0$). In this case, a curve 501 of the S parameter (reflection coefficient S) passes the right side from the center on the Smith chart 500 and draws an arc whose radius is larger than the curve 502.

In a case of the high loaded (Low Q) state illustrated in FIGS. 4(c) and 4(f), Q-factors become small, and the impedance Z at the center frequency $f(Z_{max})$ is lower than $Z_0$ ($Z(f_0)<Z_0$). In this case, a curve 503 of the S parameter (reflection coefficient S) passes the left side from the center on the Smith chart 500 and draws an arc whose radius is smaller than the curve 502.

Figure 6:
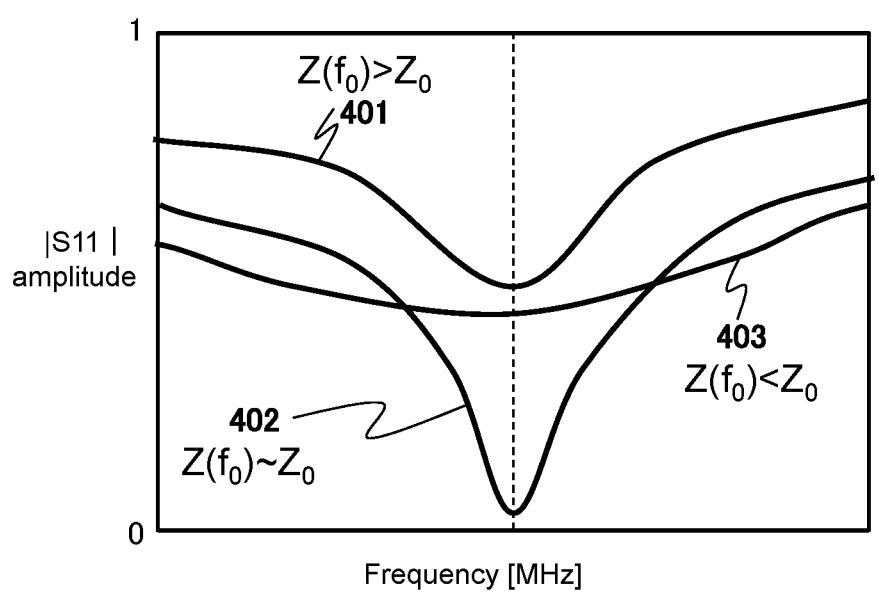
FIG. 6 illustrates changing states of the reflection coefficients in a case of different resonant impedances in the embodiments of the present invention.

FIG. 6 is a drawing in which the graphs 401, 402, and 403 of measurement values of the three reflection coefficients |S11| illustrated in FIGS. 4(a) to 4(c) are superimposed with each other. When viewing the present drawing, it is found that the curve shapes in cases where the impedance Z is high ($Z(f_0)>Z_0$) and where the impedance Z is low ($Z(f_0)<Z_0$) resemble each other and are shifted in the vertical direction as a whole. Therefore, it is examined that Q is calculated using such a slight difference.

[Q-Factor Calculation Method of Present Embodiment]

Described will be the Q-factor calculation method by the Q-factor calculation section 213 of the present embodiment. As described above, the Q-factor calculation section 213 of the present embodiment calculates Q-factors by fitting reflection coefficients acquired from amplitudes of forward waves and reflected waves to a predetermined circuit model.

As illustrated in FIGS. 4(a) to 4(f), a mode of change to frequency is different between reflection coefficients |S11| and impedances |Z11| according to the load of the RF antenna 103.

The Q-factor calculation section 213 of the present embodiment provides a plurality of different RF signals to the RF antenna 103 and measures amplitudes of the forward wave 301 and the reflected wave 302 respectively in a loaded mode during imaging i.e., in a state where the object 112 is disposed in the RF antenna 103 in a posture during imaging. Then, the amplitude of the reflected wave 302 is divided by the amplitude of the forward wave 301, and absolute values of reflection coefficients |S11| are calculated by calculating the square root in order to determine a function (S(f)) of a mode of change to frequency for the reflection coefficients |S11| represented in the graphs (401, 402, and 403).

Each channel of the RF antenna 103 can be replaced with a simple LCR (inductor, capacitor, and resistance) resonant circuit model in a narrow frequency range in the vicinity of the resonant frequency. In the present embodiment, the resonant circuit model is used in order to determine the above graphs.

Figure 7:
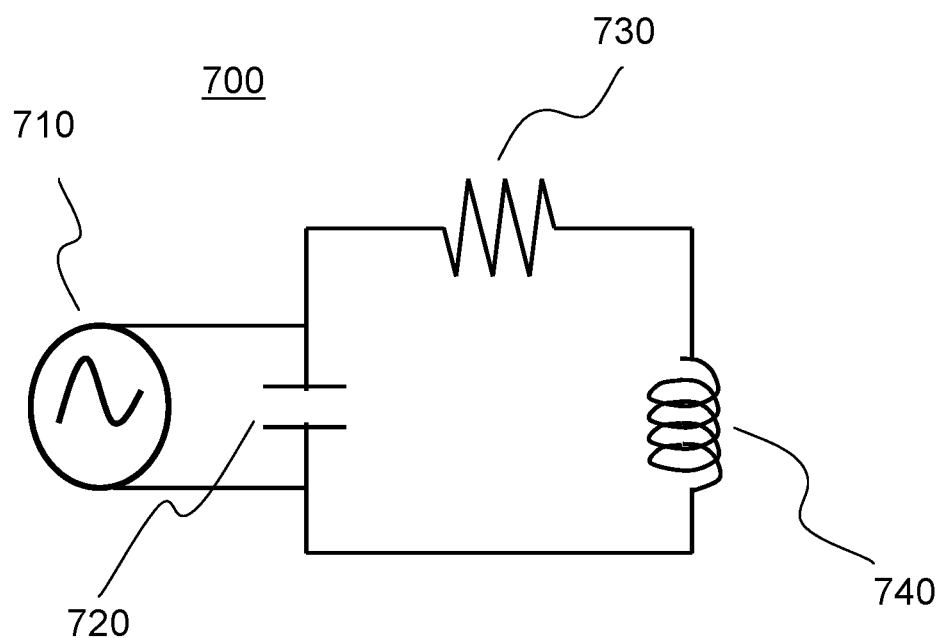
FIG. 7 is a circuit diagram of a resonant circuit model used in the embodiments of the present invention.

FIG. 7 illustrates the resonant circuit model 700. The resonant circuit model 700 comprises three circuit elements of an inductor 740, a capacitor 720, and a resistance 730 that are connected in series so as to form a loop. Furthermore, the resonant circuit model 700 is a parallel resonant circuit in which an RF frequency source 710 is connected to the capacitor 720 in parallel. It is noted that the RF frequency source 710 is equivalent to the pulse generator 201 in the RF transmission system.

The resonant circuit model 700 is a one-port circuit in which the RF frequency source 710 is connected to the capacitor 720 in parallel. Hence, a port impedance Z of the resonant circuit model 700 (an impedance Z of the RF antenna 103) can be represented by the following equation (5) using an inductance L of the inductor 740, a capacity C of the capacitor 720, and a resistance value R of the resistance 730.

$$Z = \frac{\frac{1}{C\omega i}(L\omega i + R)}{\frac{1}{C\omega i} + L\omega i + R} \tag{5}$$

By substituting the equation (5) for the equation (4-2), an S parameter (reflection coefficient) S of the resonant circuit model 700 with one port is represented by L, C, R, and ω. Here, because ω is 2πf (f is a frequency), the reflection coefficient S is represented by L, C, R, and frequencies f as shown in the following equation (6). That is, it is an f function.

$$S = \frac{2\pi f Li + R - Z_0(1 - LC \cdot (2\pi f)^2 + 2\pi f RCi)}{2\pi f Li + R + Z_0(1 - LC \cdot (2\pi f)^2 + 2\pi f RCi)} \tag{6}$$

L, C, and R can also be evaluated by providing three different frequencies f to the RF antenna 103, substituting absolute values |S11| of reflection coefficients measured respectively for those in which absolute values of both the sides of the equation (6) are calculated to acquire three equations, and then solving the equations. However, because such an exact solution has a possibility of providing a solution fa from reality in a case of data whose measurement error is large, the Q-factor calculation section 213 of the present embodiment uses a least squares method that easily provides a limited range to the solution. Specifically, effective L, C, and R values are acquired by changing the frequencies f to three or more different values, setting the respectively measured reflection coefficients |S11| as the absolute values of S of the above equation (6), and then performing least squares fitting using L, C, and R as parameters.

For example, an algorithm of general-purpose non-linear least squares fitting is used in the fitting. That is, L, C, and R values are changed in a predetermined range from predetermined default values by a predetermined change amount. Then, a solution is a set of L, C, and R values at which squares of differences between measured values and absolute values of the values acquired from the above equation (6) become the smallest.

That is, the Q-factor calculation section 213 of the present embodiment performs fitting after changing values of the respective circuit elements (the inductor 740, the capacitor 720, and the resistance 730) in order to acquire the values (L, C, and R) of the respective circuit elements. Then, Q-factors are calculated using the values of the acquired circuit elements (L, C, and R).

The Q-factors are calculated using the following equation (7).

$$\left. \begin{array}{l} \text{Re}Z_{max} = \dfrac{L}{CR} \\ \omega_0 = \dfrac{1}{\sqrt{LC}} \\ Q = \dfrac{L\omega_0}{R} = \dfrac{1}{R}\sqrt{\dfrac{L}{C}} \end{array} \right\} \quad (7)$$

It is noted that $\omega_0$ is a resonant angular velocity of a resonance system and becomes a resonant frequency $f_0$ by dividing by $2\pi$. That is, $\omega_0 = 2\pi f_0$. Therefore, these L, C, and R values can be used for calculating a real part $\text{Re}Z_{max}$ of an impedance peak value $Z_{max}$ of the RF antenna 103, a resonant frequency $f_0$ of the resonant circuit model 700, and resonant Q-factors similarly with the equation (7). In a case of substituting $\omega_0$ of the equation (7) in the equation (7), $Z_{max} = L/(CR) + i\sqrt{(L/C)}$ is evaluated. However, normally, the imaginary part is considerably smaller compared to the real part. Therefore, $\text{Re}Z_{max}$ of the real part becomes a representative parameter.

The Q-factor calculation section 213 calculates Q-factors immediately before imaging after the object 112 is disposed in the RF antenna 103. Therefore, the Q-factors acquired here are $Q_{loaded}$ being Q-factors of the RF antenna 103 in a state where the object 112 is disposed.

Although the above Q-factor calculation process performs fitting after changing values (L, C, and R) of circuit elements of the resonant circuit model 700 in order to calculate Q-factors using these values, the Q-factor calculation method is not limited to this. Q-factors may be directly calculated by performing fitting after changing $\text{Re}Z_{max}$, $\omega_0$, and Q.

The equation (7) can be rewritten into an equation evaluating L, C, and R from $\text{Re}Z_{max}$, $\omega_0$, and Q as shown in the following equation (8).

$$\left. \begin{array}{l} L = \dfrac{\text{Re}Z_{max}}{Q\omega_0} \\ C = \dfrac{1}{L\omega_0^2} = \dfrac{Q}{\text{Re}Z_{max}\omega_0} \\ R = \dfrac{\text{Re}Z_{max}}{Q^2} \end{array} \right\} \quad (8)$$

Therefore, the Q-factor calculation section 213 may perform fitting after changing Q-factors represented by values (L, C, and R) of circuit elements (the inductor 740, the capacitor 720, and the resistance 730), an impedance value $\text{Re}Z_{max}$ of the high-frequency antenna (the RF antenna 103), and a resonant angular velocity $\omega_0$ of the resonant circuit (or a resonant frequency $f_0$) in order to acquire Q-factors.

In this case, by changing $\text{Re}Z_{max}$, $\omega_0$, and Q from predetermined default values in a predetermined mode, frequencies f of reflection coefficients S of the resonant circuit model 700 are set as variables in order to acquire functions S(f) respectively. Differences between the respective functions and the acquired respective reflection coefficients |S11| are calculated in order to acquire $\text{Re}Z_{max}$, $\omega_0$, and Q of a function in which the difference is the smallest as a solution.

It is noted that parameters to be changed for fitting are not limited to a set of L, C, and R and a set of $\text{Re}Z_{max}$, $\omega_0$, and Q (or a resonant frequency $f_0$). Independent three variables may be used.

It is noted that attention needs to be paid to set default values for the above fitting. That is, as judged from the graph 402 in FIG. 4(*b*), the reflection coefficient |S11| becomes the minimum value 0 in the vicinity where an impedance Z is 50 ohms. That is, the 50-ohm point is a singular point. Therefore, in a case of changing parameter values, a $\text{Re}Z_{max}$ value is set to not 50 ohms but the default value, and two default values are provided for cases where the $\text{Re}Z_{max}$ value is greater than 50 ohms and where the $\text{Re}Z_{max}$ value is less than 50 ohms.

[Frequencies to be Changed]

Measurement time (Mtime) of reflection coefficients |S11| depends on the number of channels (nch) of the RF antenna 103, the data update time (dtime) of the monitor 202, the number of measurement frequencies (the number of measurement points in the frequency direction) (nsample). Therefore, the following equation (9) is represented by these variables.

$$M\text{time} = nch \times d\text{time} \times n\text{sample} \quad (9)$$

For example, when the RF antenna 103 has 4 channels, the data update time is 1 second (the number of data updates is 1 second), and the number of measurement points is 11, the measurement time is 44 seconds according to the above equation (9). It is requested to shorten the measurement time to approximately 6 seconds. When the data update time is reduced to 0.5 seconds and the number of measurement points is reduced to 3 points, the measurement time becomes 6 seconds.

Figure 8:
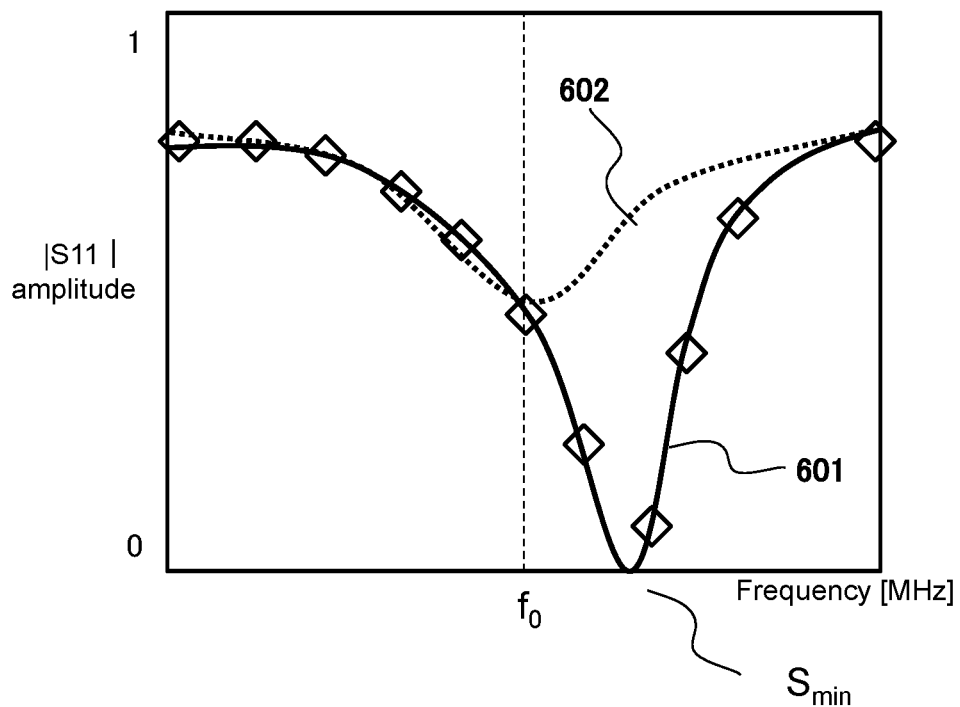
FIG. 8 illustrates a state of fitting in the embodiments of the present invention.

FIG. 8 illustrates a fitting result 601 in a case where the measurement points are 11. In the present drawing, the 11 diamonds indicate the measurement points. Fitting is performed on these measurement points using the resonant circuit model 700 in order to acquire the result 601. This is a function S(f) of a reflection coefficient S represented in the equation (6) in which f is set as a variable.

Here, reducing measurement points to 3 is tested in order to reduce measurement time. For example, fitting is performed by selecting three points: a left edge point at which the frequency is the lowest; a right edge point at which the frequency is the highest; and a resonant-frequency-$f_0$ point at the center. In this case, acquired is a curve 602 illustrated in a dotted line. That is, S(f) becomes a result different from a case of 11 points. The accuracy of Q-factors calculated from parameters acquired thus is not high.

On the other hand, fitting is performed by selecting three points: a left edge point at which the frequency is the lowest; a right edge point at which the frequency is the highest; and a frequency (minimum reflection frequency) $f(S_{min})$ being the smallest value of the fitting result 601. In this case, the result is almost the same as the fitting result 601.

Therefore, in the present embodiment, when performing fitting, the Q-factor, calculation section 213 sets frequencies f to calculate reflection coefficients |S11| as three frequencies: frequencies in the vicinity of both ends and a frequency (minimum reflection frequency) $f(S_{min})$ at which the fitting result (a function in which frequencies of the reflection coefficients |S11| are set as variables) becomes the minimum value.

For example, the three frequencies are $f_0 - 0.5$ MHz, $f(S_{min})$, and $f_0 + 0.5$ MHz. Also, the three frequencies may be upper and lower limit frequencies that the MRI apparatus 100 can use and a minimum reflection frequency $f(S_{min})$ at which a reflection coefficient of the RF antenna 103 is the smallest.

Although it is more desirable that the minimum reflection frequency $f(S_{min})$ corresponds to a resonant frequency $f_0$, there can be a case where both are shifted before the measurement due to the influence of wiring cables, a transmission/reception switch, and the like as illustrated in FIG. 8.

[Details of Process for Determining Minimum Reflection Frequency]

Next, described will be the details of the process for determining a minimum reflection frequency using the minimum reflection frequency determination section 214 of the present embodiment.

The minimum reflection frequency determination section 214 determines a minimum reflection frequency $f(S_{min})$ as described above. Here, the forward waves 301 and the reflected waves 302 are respectively measured at four or more different frequencies under loaded and unloaded states in the matching state in order to reflection coefficients |S11| respectively. Then, fitting is performed using the resonant circuit model 700 similarly to the Q-factor calculation section 213, a frequency $f(S_{min})$ at which a reflection coefficient is the smallest in the matching state is acquired, and the frequency $f(S_{min})$ is determined as the minimum reflection frequency. At this time, Q-factor($Q_{empty}$) in the unloaded state is also calculated.

Specifically, for example, L, C, and R values are determined by fitting data in the matching state to the resonant circuit model 700 using a least squares method, and a function S(f) represented in the above equation (6) is determined, which determines a frequency being a minimum point $f(S_{min})$. A Q-factor ($Q_{empty}$) in an unloaded state is calculated using the L, C, and R values acquired in the unloaded state.

In order to acquire Q-factors as accurately as possible, measurement is performed by a relatively large number of measurement frequencies (measurement points), such as 11 points, within a range of approximately ±0.5 MHz using a resonant frequency $f_0$ as a reference.

For example, in a case of the RF antenna 103 whose Q-factor has a resonant impedance peak of approximately 300 and where a resonant frequency $f_0$ is 126 MHz, $f_0/Q$ is 0.42 MHz. Approximately 5 measurement points are set for a frequency range of a resonant frequency $f_0\pm(f_0/Q)/2$, i.e., approximately 10 measurement points are set for a frequency range of approximately $f_0\pm f_0/Q$, and the resonant frequency $f_0$ is also included, which results in 11 points in total. FIG. 8 described above illustrates a state where 11 measurement points in total are set and plotted including the resonant frequency $f_0$.

It is noted that a set frequency interval is 0.084 MHz in a case where 5 points are set for the resonant frequency $f_0\pm(f_0/Q)/2$. Even if the interval is further reduced, a Q-factor evaluated by fitting hardly varies, and it is considered that the accuracy does not vary. Therefore, in a case where a resonant frequency is $f_0$ and a Q-factor of the RF antenna 103 in an unloaded state is $Q_{empty}$, it is desirable that measurement is performed at intervals of a frequency equal to or more than $f_0/Q_{empty}/5$ between upper and lower limit frequencies that the MRI apparatus 100 can use in order to determine a minimum reflection frequency using the results in the process for determining a minimum reflection frequency.

This is an example in a case where an unloaded Q-factor of the RF antenna 103 is approximately 300 in the MRI apparatus 100 having a static magnetic field of approximately 3 tesla.

In an RF antenna whose static magnetic field strength and resonant Q-factor are different, the number and range of measurement points to be needed are different respectively. That is, it is enough to perform measurement at intervals of a frequency equal to or more than a resonant frequency $f_0/Q/5$.

Although the Q-factor calculation section 213 and the minimum reflection frequency determination section 214 are different in the number of data on which fitting is to be performed, they are the same calculation function using the same algorithm. Therefore, it may be configured so that one functional unit performs both processes. That is, either of the processing units may perform both the processes.

[Process Flow for Determining Minimum Reflection Frequency]

Figure 9:
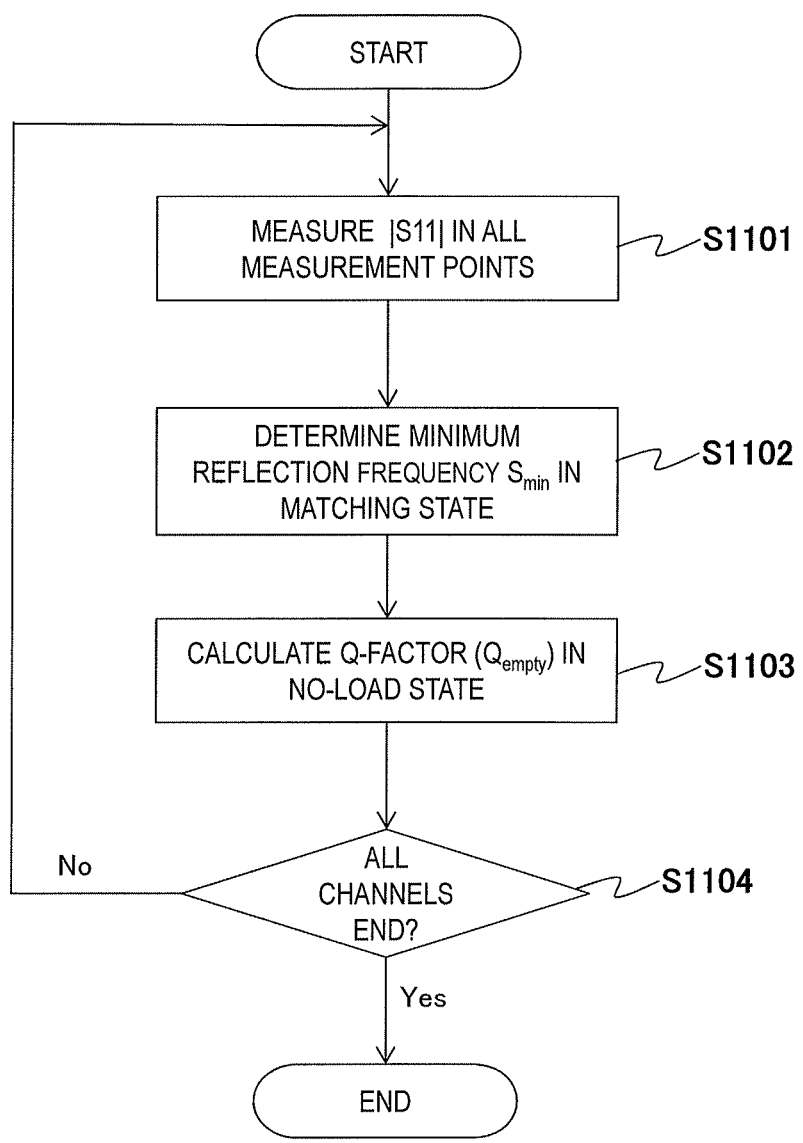
FIG. 9 is a flow chart of a minimum reflection frequency determination process in the embodiments of the present invention.

Described here will be the process flow for determining a minimum reflection frequency by the minimum reflection frequency determination section 214 of the present embodiment. FIG. 9 is a process flow for determining a minimum reflection frequency in the present embodiment. The process for determining a minimum reflection frequency in the present embodiment is executed during manufacture, installation, adjustment, maintenance, or the like as described above. The process for determining a minimum reflection frequency may be executed prior to the Q-factor calculation process described below. The process is executed in an unloaded state.

First, the minimum reflection frequency determination section 214 measures amplitudes of the forward waves 301 and the reflected waves 302 of RF pulses of four or more predetermined different frequencies (all measurement points) (full point sweep |S11| measurements at high Q (empty)) in order to calculate reflection coefficients |S11| for each frequency (Step S1101). The RF pulses of each frequency are generated from the pulse generator 201 according to a command from the supply section 212. For example, measurement is performed in a relatively large number of points, such as 11 points, within a frequency range of approximately ±0.5 MHz. it is noted that the measurement is performed in the unloaded state.

The minimum reflection frequency determination section 214 performs fitting on the acquired reflection coefficients |S11| using the resonant circuit model 700 and determines a frequency whose reflection coefficient |S11| becomes the minimum (minimum reflection frequency) $f(S_{min})$ (Step S1102).

Next, a Q-factor ($Q_{empty}$) is calculated from L, C, and R values of the resonant circuit model 700 acquired by fitting (Step S1103). The determined minimum point $f(S_{min})$ and Q-factor are recorded in association with channels.

The minimum reflection frequency determination section 214 repeats the processes of Steps S1101 and S1103 for all the channels (Step S1104).

[Q-Factor Calculation Process]

Figure 10:
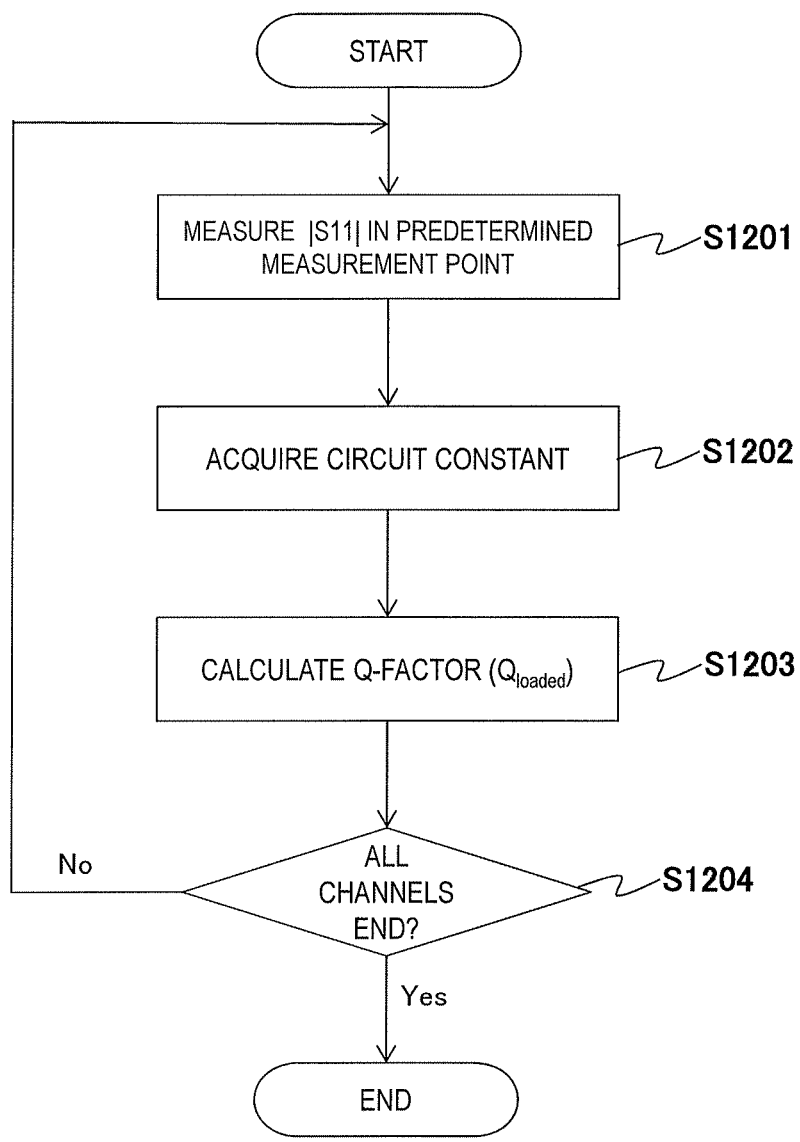
FIG. 10 is a flow chart of a Q-factor calculation process in the embodiments of the present invention.

Described next will be a flow of the Q-factor calculation process by the Q-factor calculation section 213. FIG. 10 is the process flow for the Q-factor calculation process of the present embodiment. The Q-factor calculation section 213 performs the Q-factor calculation process each time the object 112 is changed and each time an imaging site is changed during imaging in a state during imaging and a state where the object 112 is inserted. Also, the Q-factor calculation process is performed for each channel of the RF antenna 103.

The Q-factor calculation section 213 measures amplitudes of the forward waves 301 and the reflected waves 302 of the respective high-frequency pulses (RF pulses) of three or more predetermined different frequencies f to be supplied to a high-frequency antenna (the RF antenna 103) in order to calculate reflection coefficients |S11| of the respective high-frequency pulses (RF pulses) (Step S1201).

The RF pulses of the three or more predetermined different frequencies f are supplied from the pulse generator 201 according to a command from the supply section 212. Then, the Q-factor calculation section 213 acquires the amplitudes of the forward waves 301 and the reflected waves 302 respectively when the RF pulses of the respective frequencies f are supplied in order to acquire the reflection coefficients |S11|. The amplitudes of the forward waves 301 and the reflected waves 302 are measured by the monitor 202.

The Q-factor calculation section 213 acquires circuit constants by fitting each of the reflection coefficients to the predetermined resonant circuit model 700 (Step S1202). Fitting is performed using, for example, a least squares method as described above.

Here, a case of changing the inductor 740, the capacitor 720, and the resistance 730 that are circuit elements will be described as an example. Specifically, in this case, functions S(f) in which frequencies f are set as variables of reflection coefficients S of the resonant circuit model 700 are respectively acquired by changing L, C, and R values of each circuit element from predetermined default values in a predetermined manner. Then, for each of the functions, differences from each of the acquired reflection coefficients |S11| are calculated in order to acquire L, C, and R of a function whose difference is the smallest as a solution.

Then, the Q-factor calculation section 213 calculates Q-factors of a high-frequency antenna (the RF antenna 103) using the acquired circuit constants (Step S1203). Here, the acquired L, C, and R are substituted in the equation (7) in order to a Q-factor ($Q_{loaded}$).

The Q-factor calculation section 213 performs the processes of Steps S1201 and S1203 for all the channels (Step S1204) before ending the Q-factor calculation process.

It is noted that Q-factors are directly acquired by performing fitting after Step S1201 in a case of performing fitting after a Q-factor, a peak impedance value $ReZ_{max}$, and a resonant angular velocity $\omega_0$ (or a resonant frequency $f_0$) are changed.

The SAR management section 215 calculates $P_{object}$ by the above equation (2) to perform SAR management using the acquired Q-factor ($Q_{loaded}$), a Q-factor ($Q_{empty}$) in an unloaded state calculated in the process for determining a minimum reflection frequency, and a known $P_{input}$ value as described above.

Modified Example

In the above embodiment, circuit constants L, C, and R or three independent variables such as $ReZ_{max}$, $\omega_0$, and Q are changed in a predetermined range from predetermined default values by a predetermined change amount in fitting during the Q-factor calculation process and the process for determining a minimum reflection frequency in order to acquire optimal solutions. However, the fitting method is not limited to this.

For example, it may be configured so as to calculate Q-factors using one solution whose deviation is smaller from among two solutions acquired by setting two different default values and performing fitting after parameters are changed from the two default values.

For example, $ReZ_{max}$ is required not to be 50 ohms as a default value for fitting. Therefore, it may be configured so as to set two values (50+α, 50−β (α and β are positive values such as 1 to 20)) above and below 50 ohms as a default value of a peak impedance value $ReZ_{max}$ (=L/(CR)), change the $ReZ_{max}$ value so as to respectively set those values away from 50 ohms, and perform fitting twice in order to determine a smaller deviation from among the results as a solution.

Alternatively, in a case of changing L, C, and R, it may be configured so as to set L and C to the same default value and set two values only for R and similarly perform fitting twice in order to determine a smaller deviation from among the results as a solution.

Practical Example

In a case where fitting is performed using data of predetermined 11 points (11 types of frequencies) between $f_0$−0.5 MHz and $f_0$+0.5 MHz (11-point measurement) and in a case where fitting is performed in three positions (three frequencies) of $f_0$−0.5 MHz, $f_0$+0.5 MHz, and $f(S_{min})$ (3-point measurement) for one channel of the RF antenna 103, the respectively evaluated parameter values (L, R, C, $ReZ_{max}$, $f_0$, and Q) and deviations of fitting (fit deviations) are shown in a table 800 in FIG. 11.

The algorithm of general-purpose non-linear least squares fitting is used for fitting. Also, the following two types of sets (Q, $ReZ_{max}$, and $f_0$) are used as the default values for the fitting. It is noted that $f_0$ is a resonant frequency of the resonant circuit model 700.

(Q, $ReZ_{max}$, $f_0$)=(130, 45, 123.47),
(Q, $ReZ_{max}$, $f_0$)=(150, 52, 123.47)

That is, two types of default values, 45 ohms and 52 ohms, were provided above and below 50 ohms as $ReZ_{max}$. Then, a smaller deviation is selected as a correct solution from among two fitting results of a fitting result obtained by changing the $ReZ_{max}$ value from 45 ohms to a reducing direction and a fitting result obtained by changing the $ReZ_{max}$ value from 50 ohms to an increasing direction.

It is noted that there are three load types: Unloaded (Empty), Medium loaded, and Highly loaded.

The acquired Q-factors result in 267 for 11-point measurement, 272 for 3-point measurement in an unloaded state, 146 for 11-point measurement and 150 for 3-point measurement in a medium loaded state, and 52 for 11-point measurement and 54 for 3-point measurement in a highly loaded state.

As described above, the MRI apparatus 100 of the present embodiment comprises a high-frequency antenna 103 that resonates at a predetermined frequency; a supply section 212 that supplies high-frequency signals to the high-frequency antenna 103; a monitor 202 that measures amplitudes of forward waves 301 and reflected waves 302 of the high-frequency signals to be supplied from the supply section 212 to the high-frequency antenna 103; and a Q-factor calculation section 213 that calculates Q-factors of the high-frequency antenna 103 using the amplitudes, the supply section 212 supplies the high-frequency signals of three or more different frequencies to the high-frequency antenna 103, the monitor 202 measures the amplitudes respectively for the high-frequency signals of the respective supplied frequencies, and the Q-factor calculation section 213 calculates the Q-factors by fitting absolute values of reflection coefficients acquired from each of the amplitudes to a predetermined circuit model (resonant frequency model) 700.

Also, the three frequencies to be supplied by the supply section are an upper-limit frequency and a lower-limit frequency that the MRI apparatus 100 can use and a minimum reflection frequency at which a reflection coefficient of the high-frequency antenna is the smallest.

The MRI apparatus 100 of the present embodiment further comprises a minimum reflection frequency determination section 214 that determines the minimum reflection frequency, the supply section 212 supplies the high-frequency pulses of four or more predetermined different frequencies, the minimum reflection frequency determination section 214 may determine the minimum reflection frequency by fitting the reflection coefficients acquired from the respective amplitudes measured by the monitor 202 to the circuit model (resonant circuit model) 700.

The MRI apparatus 100 of the present embodiment may further comprise a specific absorption rate (SAR) management section 215 that calculates irradiation power affecting the object 112 from irradiation power by high-frequency signals to be supplied to the high-frequency antenna 103 during imaging using a Q-factor calculated by the Q-factor calculation section 213 in order to manage a specific absorption rate.

Thus, according to the present embodiment, Q-factors are calculated by performing fitting on a circuit model using values that can be measured by existing hardware of an MRI apparatus. Also, after an object is disposed during imaging, Q-factors can be calculated by transmitting RF pulses of at least three frequencies. Therefore, accurate Q-factors can be acquired only with existing hardware without mounting an expensive measuring device newly and without considerably extending imaging time from the normal imaging time.

Therefore, according to the present embodiment, a just enough SAR can be acquired with accurate Q-factors, which can realize highly accurate and efficient SAR management.

In SAR management in the conventional MRI imaging, a SAR tends to be overestimated by adopting a method of estimating the SAR simply, which results in extending the imaging time. Alternatively, in order to estimate the SAR accurately, required is Q-factor measurement in all the channels of the RF antenna 103 i.e., measurement of amplitudes and phases of forward waves and reflected waves for each imaging site of an object. However, the Q-factor measurement requires an expensive measuring device and takes a long time.

According to the present embodiment, problems caused by such a conventional technique can be solved, and Q-factors can be acquired accurately without adding new hardware to the MRI apparatus 100 and increasing a burden on a patient, which enables accurate SAR management using the accurate Q-factors.

An RF transmission system of the above respective embodiments is not limited to an MRI apparatus and can be applied to all the devices that need to manage transmission power of electromagnetic waves and a SAR at which the transmission power affects a human body using the electromagnetic waves with frequencies between a few kHz and a few GHz.

The data processing unit 105 of the present embodiment is provided with a CPU, a memory, and a storage device. Then, each function that the data processing unit 105 realizes is realized by that the CPU of the data processing unit 105 loads a program stored in the storage device into the memory before execution. All or a part of the functions may be realized by hardware such as ASIC (Application Specific Integrated Circuit) and FPGA (Field-programmable Gate Array). Various data to be used for processing each function and various data to be generated during the process are stored in the storage device.

It is noted that the embodiments of the present invention are not limited to the above respective embodiments and various additions and changes can be performed in a range without departing from the gist of the invention.

REFERENCE SIGNS LIST

100: MRI apparatus
101: magnets
102: gradient magnetic field coils
103: RF antenna
104: transceiver
105: data processing unit
106: transmission/reception cables
107: gradient magnetic field control cable
108: display device
109: gradient magnetic field power source
111: bed
112: object
201: pulse generator
202: monitor
203: power amplifier
212: supply section
213: Q-factor calculation section
214: minimum reflection frequency determination section
215: SAR management section
301: forward waves
302: reflected waves
401: graph of a reflection coefficient
402: graph of a reflection coefficient
403: graph of a reflection coefficient
411: graph of an impedance
412: graph of an impedance
413: graph of an impedance
500: Smith chart
501: curve
502: curve
503: curve
601: fitting result
602: fitting result
700: resonant circuit model
710: RF frequency source
720: capacitor
730: resistance
740: inductor
800: table

The invention claimed is:

1. A magnetic resonance imaging apparatus comprising:
a high-frequency antenna that resonates at a predetermined frequency;
a supply section that supplies high-frequency signals to the high-frequency antenna;
a monitor that measures amplitudes of forward waves and reflected waves of the high-frequency signals to be supplied from the supply section to the high-frequency antenna; and
a Q-factor calculation section that calculates Q-factors of the high-frequency antenna using the amplitudes,
wherein the supply section supplies the high-frequency signals of three or more different frequencies to the high-frequency antenna,
the monitor measures the amplitudes respectively for the high-frequency signals of the respective supplied frequencies, and
the Q-factor calculation section calculates the Q-factors by fitting absolute values of reflection coefficients acquired from each of the amplitudes to a predetermined circuit model, and wherein included are three frequencies of the high-frequency signals to be supplied by the supply section: an upper-limit frequency that the MRI apparatus can use; a lower-limit frequency; and a minimum reflection frequency at which the reflection coefficients of the high-frequency antenna are the smallest.

2. The magnetic resonance imaging apparatus according to claim 1, further comprising:
a minimum reflection frequency determination section that determines the minimum reflection frequency,
wherein the supply section supplies the high-frequency pulses of four or more predetermined different frequencies, and
the minimum reflection frequency determination section determines the minimum reflection frequency by fitting absolute values of the reflection coefficients acquired from the respective amplitudes measured by the monitor 202 to the circuit model.

3. A magnetic resonance imaging apparatus comprising:
a high-frequency antenna that resonates at a predetermined frequency;
a supply section that supplies high-frequency signals to the high-frequency antenna;
a monitor that measures amplitudes of forward waves and reflected waves of the high-frequency signals to be supplied from the supply section to the high-frequency antenna; and
a Q-factor calculation section that calculates Q-factors of the high-frequency antenna using the amplitudes,
wherein the supply section supplies the high-frequency signals of three or more different frequencies to the high-frequency antenna,
the monitor measures the amplitudes respectively for the high-frequency signals of the respective supplied frequencies, and
the Q-factor calculation section calculates the Q-factors by fitting absolute values of reflection coefficients acquired from each of the amplitudes to a predetermined circuit model, and
wherein the high-frequency antenna is provided with a plurality of channels,
the monitor monitors the amplitudes of the respective channels, and
the Q-factor calculation section calculates the Q-factors for each of the channels.

4. The magnetic resonance imaging apparatus according to claim 2,
wherein the high-frequency antenna is provided with a plurality of channels,
the monitor monitors the amplitudes of the respective channels, and
the minimum reflection frequency determination section determines the minimum reflection frequency for each of the channels.

5. A magnetic resonance imaging apparatus comprising:
a high-frequency antenna that resonates at a predetermined frequency;
a supply section that supplies high-frequency signals to the high-frequency antenna;
a monitor that measures amplitudes of forward waves and reflected waves of the high-frequency signals to be supplied from the supply section to the high-frequency antenna; and
a Q-factor calculation section that calculates Q-factors of the high-frequency antenna using the amplitudes,
wherein the supply section supplies the high-frequency signals of three or more different frequencies to the high-frequency antenna,
the monitor measures the amplitudes respectively for the high-frequency signals of the respective supplied frequencies, and
the Q-factor calculation section calculates the Q-factors by fitting absolute values of reflection coefficients acquired from each of the amplitudes to a predetermined circuit model, and
wherein the Q-factor calculation section calculates the Q-factors using the amplitudes measured at a load during imaging.

6. The magnetic resonance imaging apparatus according to claim 2,
wherein the minimum reflection frequency determination section determines the minimum reflection frequency using the amplitudes measured in a matching state and calculates the Q-factors using the amplitudes measured in an unloaded state.

7. The magnetic resonance imaging apparatus according to claim 1,
wherein the circuit model is a parallel resonant circuit model comprising three circuit elements of an inductor, a capacitor, and a resistance, and
the Q-factor calculation section performs the fitting by changing values of the respective circuit elements in order to acquire the values of the respective circuit elements and calculates the Q-factors using the values of the circuit elements.

8. The magnetic resonance imaging apparatus according to claim 1,
wherein the circuit model is a parallel resonant circuit model comprising three circuit elements of an inductor, a capacitor, and a resistance, and
the Q-factor calculation section performs fitting after changing the Q-factors represented by values of the circuit elements, an impedance peak value of the high-frequency antenna, and a resonant frequency of the circuit model in order to acquire the Q-factors.

9. The magnetic resonance imaging apparatus according to claim 2,
wherein the four or more different frequencies are, between an upper-limit frequency and a lower-limit frequency that the magnetic resonance imaging apparatus can use, determined so that each frequency interval is equal to or more than a value for which a resonant frequency $f_0$ was divided by a value of 5 times the Q-factors in an unloaded state.

10. A magnetic resonance imaging apparatus comprising:
a high-frequency antenna that resonates at a predetermined frequency;
a supply section that supplies high-frequency signals to the high-frequency antenna;
a monitor that measures amplitudes of forward waves and reflected waves of the high-frequency signals to be supplied from the supply section to the high-frequency antenna; and
a Q-factor calculation section that calculates Q-factors of the high-frequency antenna using the amplitudes,
wherein the supply section supplies the high-frequency signals of three or more different frequencies to the high-frequency antenna,
the monitor measures the amplitudes respectively for the high-frequency signals of the respective supplied frequencies, and the Q-factor calculation section calculates the Q-factors by fitting absolute values of reflection coefficients acquired from each of the amplitudes to a predetermined circuit model, and wherein the Q-factor calculation section sets two different default values and performs fitting after parameters are changed from the two default values in order to calculate the Q-factors using one solution whose deviation is smaller from among the two acquired solutions.

11. The magnetic resonance imaging apparatus according to claim 10, wherein a parameter that sets two different default values is an impedance of the high-frequency antenna, and wherein the two different default values are set to values above and below 50 ohms.

12. The magnetic resonance imaging apparatus according to claim 1, wherein a specific absorption rate management section is further provided to calculate irradiation power that affects an object from irradiation power by high-frequency signals to be supplied to the high-frequency antenna during imaging using the Q-factor calculated by the Q-factor calculation section in order to control a specific absorption rate.

* * * * *